(12) United States Patent
Krone

(10) Patent No.: US 10,398,549 B2
(45) Date of Patent: Sep. 3, 2019

(54) SYSTEM AND METHOD FOR TRANSCATHETER HEART VALVE PLATFORM

(71) Applicant: Abbott Cardiovascular Systems Inc., Santa Clara, CA (US)

(72) Inventor: Ryan T. Krone, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 590 days.

(21) Appl. No.: 15/071,077

(22) Filed: Mar. 15, 2016

(65) Prior Publication Data

US 2017/0265994 A1  Sep. 21, 2017

(51) Int. Cl.
*A61F 2/24* (2006.01)
(52) U.S. Cl.
CPC ............ *A61F 2/243* (2013.01); *A61F 2/2409* (2013.01); *A61F 2/2436* (2013.01); *A61F 2/2418* (2013.01); *A61F 2250/0071* (2013.01)
(58) Field of Classification Search
CPC ....... A61B 17/11; A61B 17/068; A61F 2/243; A61F 2/2436
See application file for complete search history.

(56) References Cited

U.S. PATENT DOCUMENTS

| | | | |
|---|---|---|---|
| 6,402,780 B2 | 6/2002 | Williamson, IV et al. |
| 7,455,677 B2 | 11/2008 | Vargas et al. |
| 7,993,394 B2 | 8/2011 | Hariton et al. |
| 8,118,866 B2 | 2/2012 | Herrmann et al. |
| 8,449,599 B2 | 5/2013 | Chau et al. |
| 8,579,964 B2 | 11/2013 | Lane et al. |
| 8,852,272 B2 | 10/2014 | Gross et al. |
| 9,034,032 B2 | 5/2015 | McLean et al. |
| 2005/0075584 A1 | 4/2005 | Cali |
| 2005/0075730 A1 | 4/2005 | Myers et al. |

(Continued)

FOREIGN PATENT DOCUMENTS

| | | |
|---|---|---|
| FR | 2828091 A1 | 2/2003 |
| WO | 2013059743 A1 | 4/2013 |
| WO | 2013155474 A1 | 10/2013 |

OTHER PUBLICATIONS

EPO, PCT Written Opinion of the International Searching Authority, sheets 1-5.

*Primary Examiner* — Melanie R Tyson
(74) *Attorney, Agent, or Firm* — Baker Botts L.L.P.

(57) ABSTRACT

A method for delivering a platform for reinforcing an annulus of a mitral valve: Passing a catheter having a sheath covering a tube formed from a metal into the left atrium, the tube including: an annular portion defining at least one opening, a plurality of upper elements attached to an upper perimeter of the annular portion and extending axially, and a plurality of lower elements attached to a lower perimeter of the annular portion. Inserting the tube into the annulus of the mitral valve; withdrawing the sheath, but leaving the sheath covering the annular portion and the upper elements; bending the lower elements until the lower elements extend radially so as to be positioned beneath the mitral valve; then withdrawing the sheath from covering the annular portion and the upper elements; bending the upper elements until the upper elements extend radially so as to be positioned above the mitral valve.

22 Claims, 10 Drawing Sheets

(56) References Cited

U.S. PATENT DOCUMENTS

| | | |
|---|---|---|
| 2008/0021546 A1 | 1/2008 | Patz et al. |
| 2012/0179244 A1 | 7/2012 | Schankereli et al. |
| 2013/0172978 A1 | 7/2013 | Vidlund et al. |
| 2013/0310923 A1* | 11/2013 | Kheradvar ............ A61F 2/2439 623/2.11 |
| 2014/0005769 A1 | 1/2014 | Tran et al. |
| 2014/0012367 A1 | 1/2014 | Venkatasubramanian et al. |
| 2014/0358222 A1 | 12/2014 | Gorman, III et al. |

* cited by examiner

SYSTEM AND METHOD FOR TRANSCATHETER HEART VALVE PLATFORM

BACKGROUND

The present invention relates to mitral valve prosthetic devices and, more particularly, to platforms into which mitral valve prosthetic devices may be deployed via a transcatheter approach.

The use of a catheter-based percutaneous valved stent has been shown to be feasible in replacing in humans both the pulmonic and the aortic valves. The pulmonic valve was the first to be successfully replaced by a percutaneous approach and is the furthest along in development. There are currently two aortic valve products in clinical trials and more in development that are deployed percutaneously.

In addition to the percutaneous catheter-based aortic valve replacement devices there are three other types of replacement valve prosthesis known to the applicants that use different technologies. One known technology, named the Transcatheter Mitral Valve Implantation (TMVI), is being developed by CardiAQ Valve Technologies (CVT). This design is fundamentally a shape memory stent. A second known technology is being developed by EndoValve. The EndoValve design is not stent based but relies on a tripod anchoresk system with a central supporting strut. A device to be used with this technology will be introduced by minimally invasive surgical techniques. A third known minimally invasive mitral valve replacement device is being developed by the University of Kiel in Germany. Their design is stent based but requires placement through the apex of the left ventricle (LV), which can be relatively dangerous particularly in patients with CHF and IMR.

There are also a large group of percutaneous mitral valve repair devices that have been developed to date. The majority of these devices have tried to exploit the proximity of the coronary sinus to the mitral valve annulus to perform some type of "annuloplasty" to limit mitral regurgitation. The basic premise behind all of them is to place a device in the coronary sinus that will shrink the valve orifice and thus decrease mitral regurgitation. However, many of these systems are still under development, and are difficult to implant.

There is a substantial need for percutaneous mitral valve replacement technologies that are appropriately configured to account for the dimensions and geometry of the mitral valve. It would be advantageous to have a device that can be deployed percutaneously and/or transapically to create a platform at the mitral valve position that reduces the diameter to an appropriate and uniform size for subsequent percutaneous or transapical implantation of a valved-stent.

The present inventors have addressed the above needs by providing for a mitral valve prosthesis that may be percutaneously or transapically deployed in at least two stages. In a first stage, the subject of the present invention, a mitral annular platform adapted for percutaneous or transapical delivery is delivered to and anchored in the mitral valve annulus. In the second stage, which may include a known valved-stent mitral valve prosthetic device adapted for percutaneously or transapical delivery may be delivered to the mitral valve annulus for mounting in the mitral annular ring platform. The approach adopted by the present invention provides a consistent platform, and this may subsequently be used for accepting valved-stent mitral valve prosthetic devices from different vendors.

Introduction to delivering an implant within the heart.

By way of introduction to the field of the invention, and referring to FIG. 1, the heart 102 is a pump, the outlet of which is the aorta, including the descending aorta 104, which is a primary artery in the systemic circulation. The circulatory system, which is connected to the heart 102 further comprises the return, or venous, circulation. The venous circulation comprises the superior vena cava 108 and the inferior vena cava 106. The right and left jugular veins, 110 and 112, respectively, and the subclavian vein 114 are smaller venous vessels with venous blood returning to the superior vena cava 108. The right and left femoral veins, 116 and 118 respectively, return blood from the legs to the interior vena cava 106. The veins carry blood from the tissues of the body back to the right heart, which then pumps the blood through the lungs and back into the left heart. The arteries of the circulatory system carry oxygenated blood (not shown) from left ventricle of the heart 102 to the tissues of the body.

FIG. 2, is a cross-sectional illustration of the heart 102, showing the atrial septum 504. The distal region 302 of a catheter 300, substantially located within the right atrium 202, is shown with its longitudinal axis perpendicular to the atrial septum 504. The distal sheath 304, surrounding the catheter 300 is shown resident within the inferior vena cava 106. A septal penetrator 500 is shown extended through a puncture 502 in the atrial septum 504 and is routed into the left atrium 404. The septal penetrator 500 is a needle or axially elongate structure with a sharp, pointed distal end. The septal penetrator 500 is actuated at the distal end of the catheter 300. The septal penetrator 500 is operably connected to a control mechanism such as a button, lever, handle, trigger, etc., which is affixed, permanently or removably, at the proximal end of the catheter (not shown) by way of a linkage, pusher rod, or the like that runs the length of the catheter. Penetration of the septal wall 504 is known in the art, and may be used to position an implant such as a prosthetic mitral valve 410 in a manner that is shown in FIG. 3 wherein the existing leaflets 402 of the mitral valve are pushed aside and the exemplary prosthetic mitral valve 410 is deployed, thereby totally disabling the natural leaflets.

Thus it is known how to position a distal tip of a delivery catheter above the mitral valve of a patient through minimally invasive means. The present invention uses such known methods and systems, and uses them as described below in order to address shortcomings noted in the prior art with regard to placement of a mitral annular platform.

SUMMARY OF THE INVENTION

In some embodiments, the invention is a method for delivering a platform for reinforcing an annulus of a mitral valve in a heart of a patient, the heart including a right atrium, a left atrium, and a septum separating the right atrium from the left atrium. The method comprises passing, via a femoral artery of a patient, a catheter having a sheath covering a tube formed from a metal into the right atrium then through the septum into the left atrium, the tube being cut to define a structure that includes an annular portion defining a bore and an axis that extends along the bore, and further defining at least one opening in a circumferential surface of the annular portion, a plurality of upper elements attached to an upper perimeter of the annular portion and extending axially, and a plurality of lower elements attached to a lower perimeter of the annular portion and extending axially. Once the catheter has been so inserted, the tube is inserted into the annulus of the mitral valve. Then the sheath is withdrawn from covering the lower elements, but leaving the sheath covering the annular portion and the plurality of upper elements. Then, the plurality of lower elements are bent by imparting a plastic deformation to the metal until the plurality of lower elements extend radially so as to be positioned beneath the mitral valve. Thereafter, the sheath is withdrawn from covering the annular portion and the plurality of upper elements, whereafter, the plurality of upper elements are bent by imparting a plastic deformation to the metal until each of the plurality of upper elements extends radially so as to be positioned above the mitral valve.

In some embodiments, the annular portion occupies a first cylindrical profile having a first diameter, and the plurality of lower elements prior to being bent occupy a second cylindrical profile having a second diameter smaller than the first diameter, and wherein bending the plurality of lower elements includes moving a piston distally through the annular portion and engaging each of the plurality of lower elements with the piston, the piston having a third diameter greater than the second diameter. In embodiments, moving a piston distally through the annular portion and engaging each of the plurality of lower elements with the piston is simultaneously accompanied by restraining the first diameter of the annular portion against expansion. In embodiments, restraining the annular portion against expansion of the first diameter includes positioning a resilient ring around the lower perimeter of the annular portion, and in some embodiments, positioning a resilient ring includes positioning a distal end of the sheath around the lower perimeter of the annular portion.

In some embodiments, the method of the invention includes expanding the first diameter of the annular portion by imparting a plastic deformation to the metal. In this case, in further embodiments, expanding the first diameter of the annular portion includes expanding the first diameter until the annular portion is in contact with the annulus of the mitral valve along a continuous circumference of the annular portion. In some embodiments, expanding the first diameter of the annular portion includes expanding the third diameter of the piston. In yet further embodiments, bending the plurality of upper elements includes applying an axially oriented force on each of the plurality of upper elements. Some embodiments may include the further step of applying a force having a radially outward component to each of the plurality of upper elements. In some embodiments, applying a force having a radially outward component to each of the plurality of upper elements includes applying a moving force to a proximal extremity of each of the plurality of upper elements. In other embodiments, applying an axially oriented force includes applying a force to a proximal extremity of each of the plurality of upper elements. In yet other embodiments, applying an axially oriented force includes restraining the annular portion against distal movement, and in some embodiments, restraining the annular portion against distal movement includes inserting a pin into the at least one opening. These embodiments provide a novel and useful method for delivering a platform for reinforcing an annulus of a mitral valve in a heart of a patient.

In another embodiment, the invention is a system for delivering a platform to support a prosthetic mitral valve in a patient's heart. The system comprises a delivery catheter that includes a slidable sheath, a tube positioned within the slidable sheath and being cut to define a structure that includes: an annular portion defining a bore and an axis that extends along the bore, and further defining at least one opening in a circumferential surface of the annular portion; a plurality of upper elements attached to an upper perimeter of the annular portion and extending axially; and a plurality of lower elements attached to a lower perimeter of the annular portion and extending axially. A piston configured to slide within the tube is provided, the piston defining a lumen that receives at least one pin configured to slide out of the lumen so as to pass through the at least one opening. In some embodiments, the at least one pin is two pins, and the two pins are separated from each other by a spring configured to urge the two pins apart from each other. In some embodiments, each of the two pins is attached to a retraction wire that extends inside the lumen, the retraction wire being attached to each of the two pins, whereby the two pins are urged towards each other when the retraction wire is pulled proximally. In some embodiments, the slidable sheath includes a resilient ring at a distal end of the slidable sheath. In further embodiments, the resilient ring is made of metal. In yet other embodiments, the annular portion occupies a first cylindrical profile having a first diameter, and the plurality of lower elements occupy a second cylindrical profile having a second diameter smaller than the first diameter. In some embodiments, the piston has an outer circumferential surface having a third diameter that is smaller than the first diameter but larger than the second diameter, whereby distal movement of the piston applies a force against the plurality of lower elements thus to urge each of the plurality of lower elements to bend away from the axis. In some embodiments, the piston includes a means for causing the outer circumferential surface to expand. In other embodiments, the system includes a means for applying a distal force against a proximal end of each of the plurality of upper elements and thus to urge the plurality of upper elements to bend away from the axis. The embodiments thus described provide a novel and useful system for delivering a platform to support a prosthetic mitral valve in a patient's heart.

DETAILED DESCRIPTION OF THE PREFERRED EMBODIMENTS

In some embodiments, as described with reference to the figures, the invention comprises a system and method for installing a platform or an annulus to reinforce the natural annulus of a diseased mitral valve in a patient.

Figure 1:
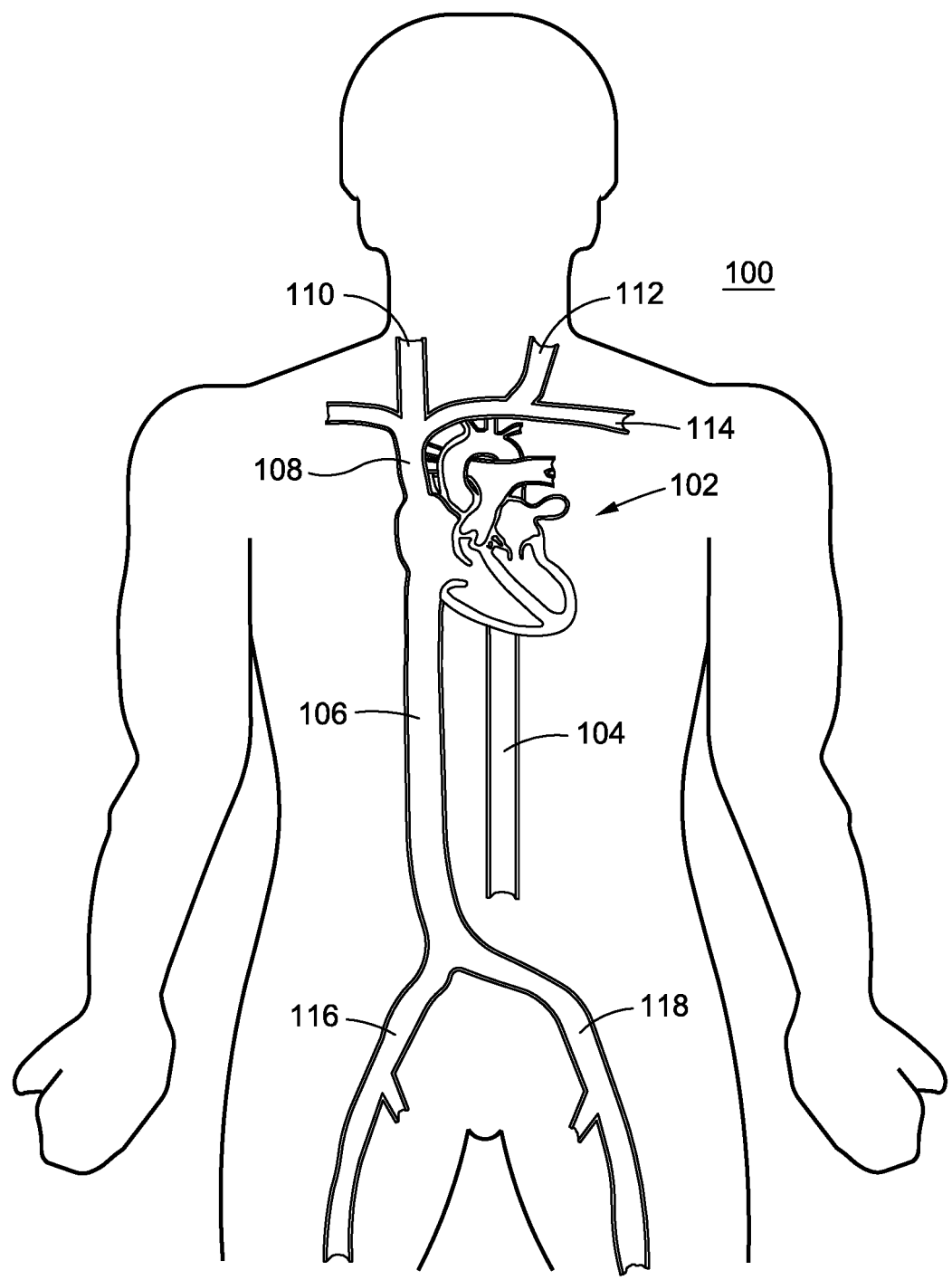
FIG. 1 is a front view schematic representation of the human venous circulatory system including the heart and the great veins.
Figure 2:
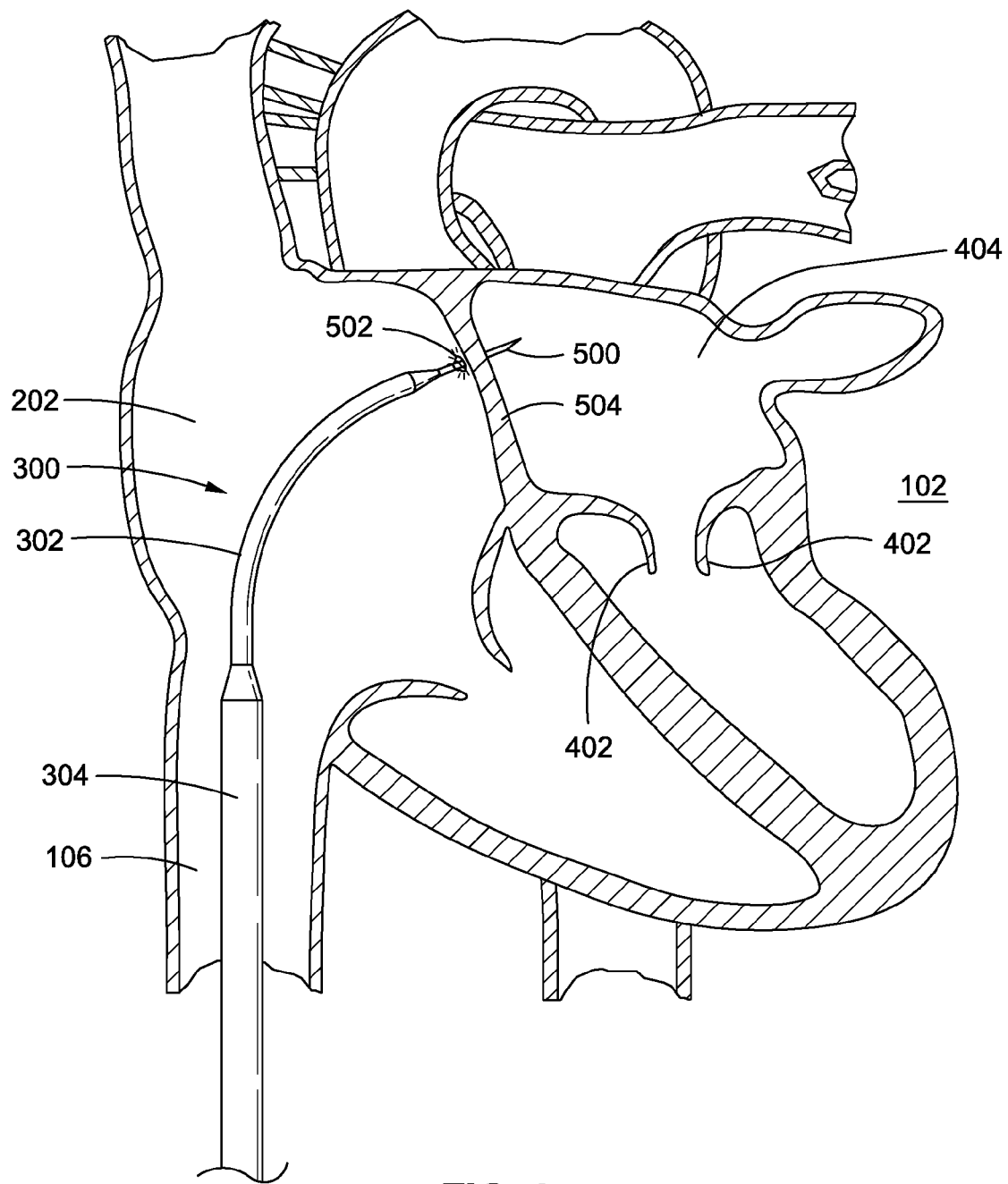
FIG. 2 is a cross-sectional illustration of the heart with a catheter positioned at the atrial septum and a septal penetrator advanced across the atrial septum into the left atrium.
Figure 3:
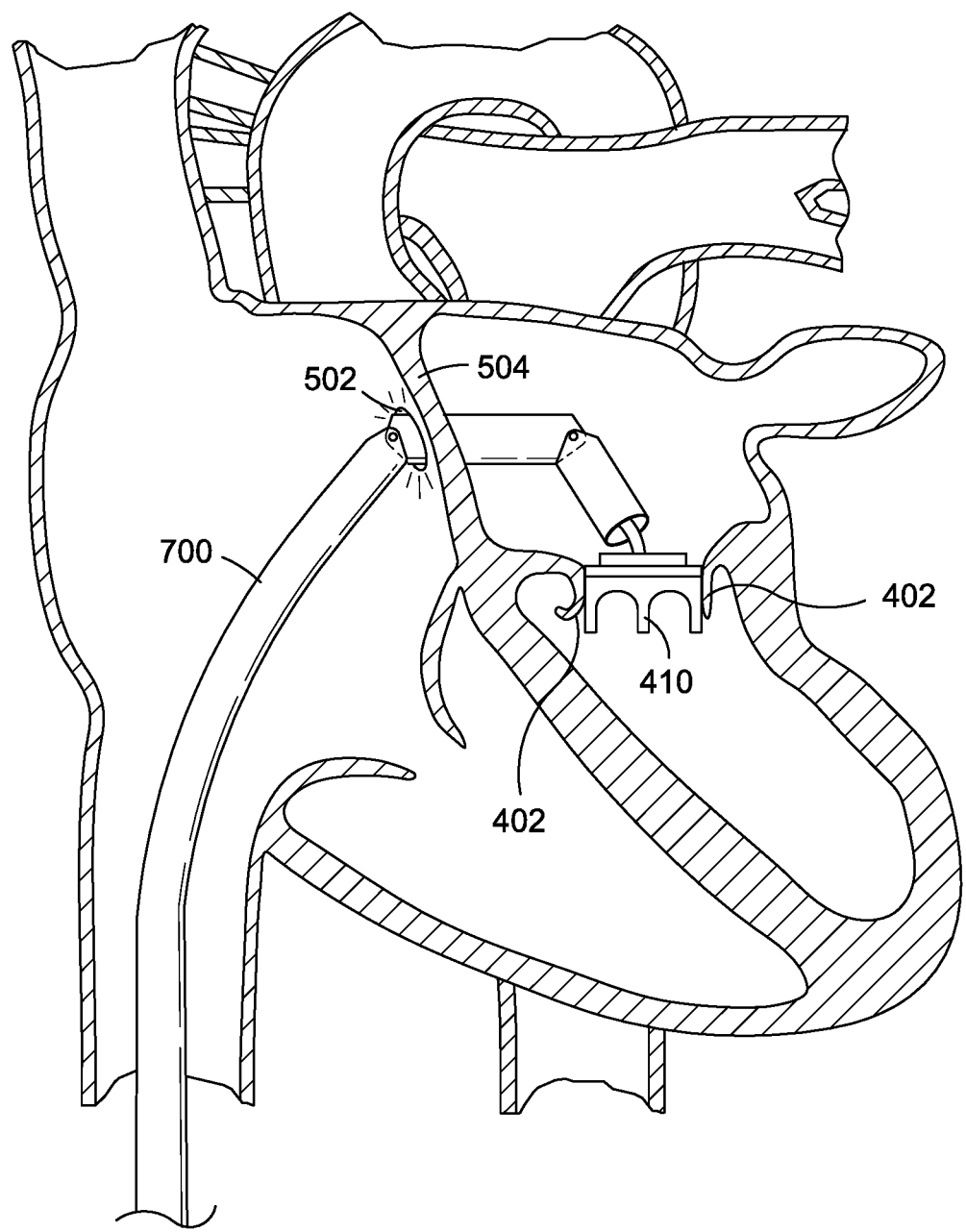
FIG. 3 is a cross-sectional illustration of the heart with a catheter advanced into the right atrium and delivering an implant.
Figure 4:
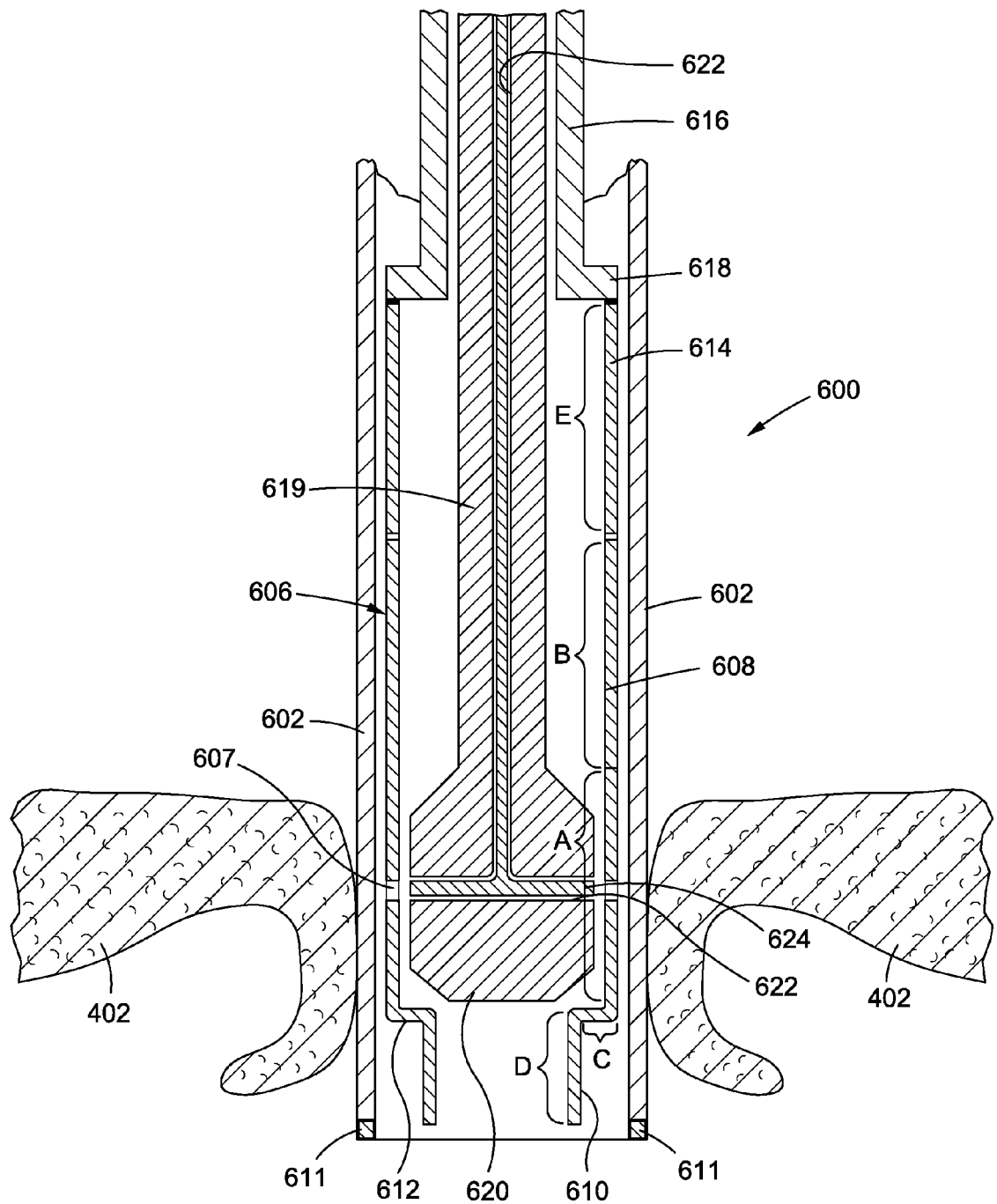
FIG. 4 is a sectional view taken through a distal end of catheter having features of an embodiment of the invention, where the distal end has been inserted between the leaflets of a mitral valve of a patient.

Turning now to an embodiment of the invention, and referring to FIG. 4, a distal end of a delivery catheter 600 is shown, extending downwardly and inserted between the leaflets 402 of a mitral valve in a patient's heart using known technique. The external sheath of the catheter may be of a kind that is known in the art, for delivering an implant into the left ventricle of the heart of a patient.

At its distal end, the catheter is surrounded by a sheath 602 that is slidably retractable in relation to other internal elements of the catheter. (Stated differently, other internal elements of the catheter are distally slidable in relation to the sheath.) Held within the sheath is a stent-like tube 606 in a compressed condition, which, at this stage before deployment is substantially cylindrical in shape. Like some forms of stent, the tube is formed from a metal that is metallurgically prepared so that, when it is expanded and bent during deployment, it is plastically deformed and retains its bent shape after the bending force has been removed.

Figure 9:
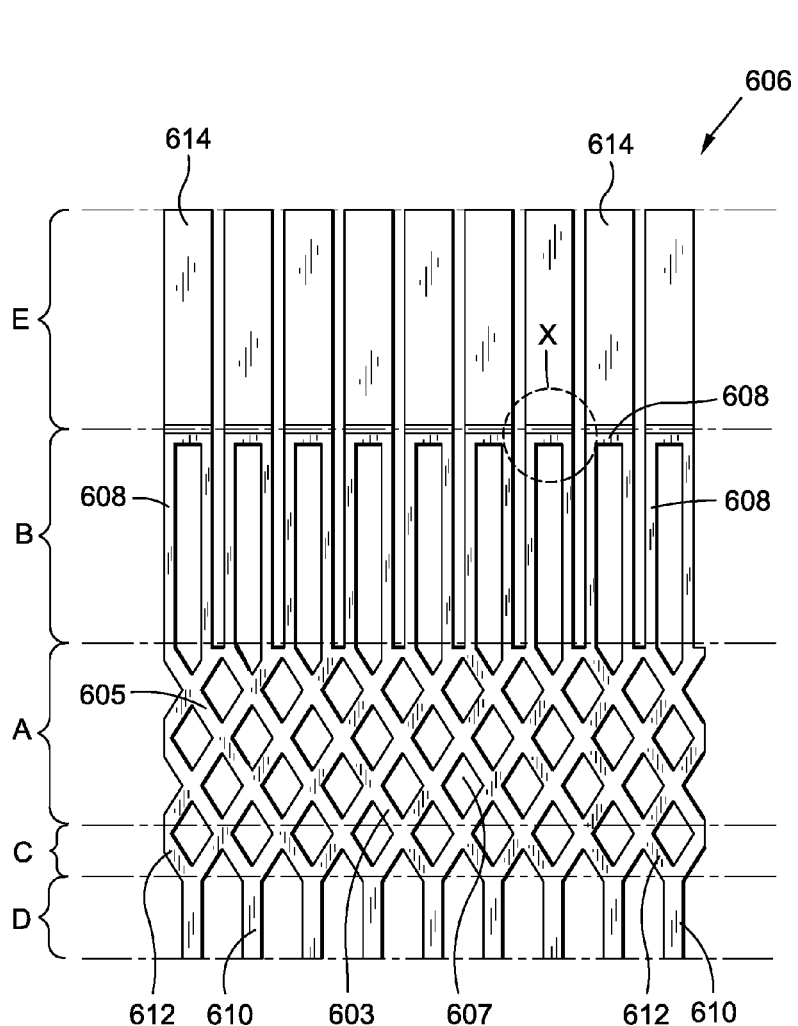
FIG. 9 is a "rollout" view of a cylindrical component having features of an embodiment of the invention.
Figure 10:
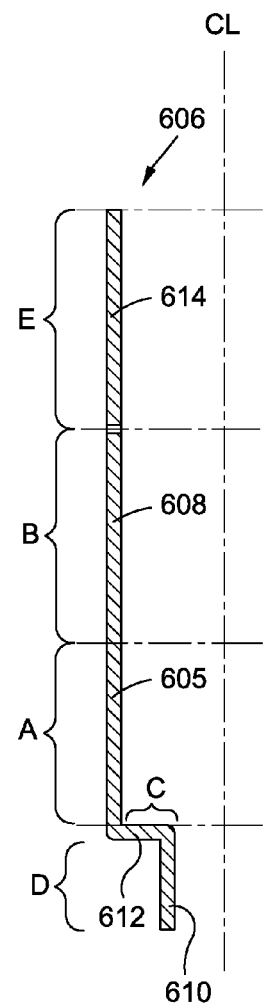
FIG. 10 is a sectional view of a left half of the cylindrical component shown in FIG. 9, after having been bent according to an embodiment of the invention.

Turning briefly to a fuller description of the tube 606, FIG. 9 shows, in vertical "rollout" format, an embodiment of the tube 606 in its cylindrical condition just after it has been laser cut using known techniques of stent fabrication. FIG. 10 shows a vertical sectional view through one side of the tube after it has been bent (as described more fully below) prior to insertion into the catheter 600.

The tube 606 is configured according to the following principles. Much like a stent, the tube is formed from struts, bends, and links, cut from a metal tube using a known laser cutting technique. In Section A (as indicated by the bracket in the figures), the tube consists of a mesh of struts 605 that intersect and are interconnected at joints. Openings 607 are found between the struts 605. Section A is also referred to herein as an annular portion, and it will substantially retain the profile of an annulus even after final deployment of the tube in the heart of a patient.

Positioned above Section A is Section B, which consists of a plurality of upper flange elements 608. These may in some embodiments be formed into a closed loop, as shown in FIG. 9. Importantly, each upper flange element 608 is not interconnected with another upper flange element. The upper flange elements are configured to deform free of each other.

Below Section A is Section C, which is a transition zone between Section A and Section D. Section D comprises a plurality of lower flange elements 610. Like the upper flange elements, these are also configured to deform independently of each other. Section C comprises a plurality of transition elements 612, which connect the struts 605 of Section A with the lower flange elements 610 of Section D. The transition elements 612 are sloped at an angle to the axis of the tube, to accommodate a compression of the lower flange elements as will be described below. Importantly, each lower flange element 610 is not interconnected with another lower flange element. The lower flange elements are configured to deform free of each other.

Above Section B is section E, which comprises a plurality of push rods 614. As will be described in more detail below, the push rods are each configured to pair with and contact an upper flange element 608, and to apply a compressive load onto the top of the upper flange elements 608 to force them radially outwardly during formation of flanges on the delivered annular portion.

Before the tube 606 is loaded into the catheter, two bending operations are performed on its structure which deforms the tube from a pure cylindrical form to a compound cylindrical form. First, the lower flange elements 610 found in Section D are bent radially outwardly at substantially a right angle to the axis of the tube. Second, the transition elements 612 are bent radially inwardly at substantially a right angle to the axis of the tube. The resulting configuration is shown in FIG. 10. The second bending operation causes movement by the lower flange elements 610 so that they are once again pointing axially downwardly, as shown in FIG. 10, and occupy a cylindrical space that has a smaller diameter than the remainder of the tube. The transition elements 612 extend radially inwardly, to connect the two portions of the tube 606 together.

The tube 606, once it is bent into the configuration shown in FIG. 10, is then loaded into the catheter 600, as shown in FIG. 4. Above the tube is a pusher element 616 that is operable from the proximal end of the catheter 600. The pusher element 616 has feet 618 that are configured to make contact with and to apply a compressive load on the push rods 614 of the tube when a distal movement of the pusher element from the proximal end of the catheter causes a distal movement of the feet 618 at the distal end.

Slidable within a lumen in the pusher element 616 is an expander element, which is operable via a rod 619 from the proximal end of the catheter. At the distal end of the expander element is a piston 620 which has an external diameter that fits snugly within the internal diameter of the mesh of struts 605 that form Section A of the tube (FIG. 4). The external diameter of the piston is larger than the internal diameter of the lower flange elements 610 that form Section D of the tube as shown in FIG. 4.

Figure 5:
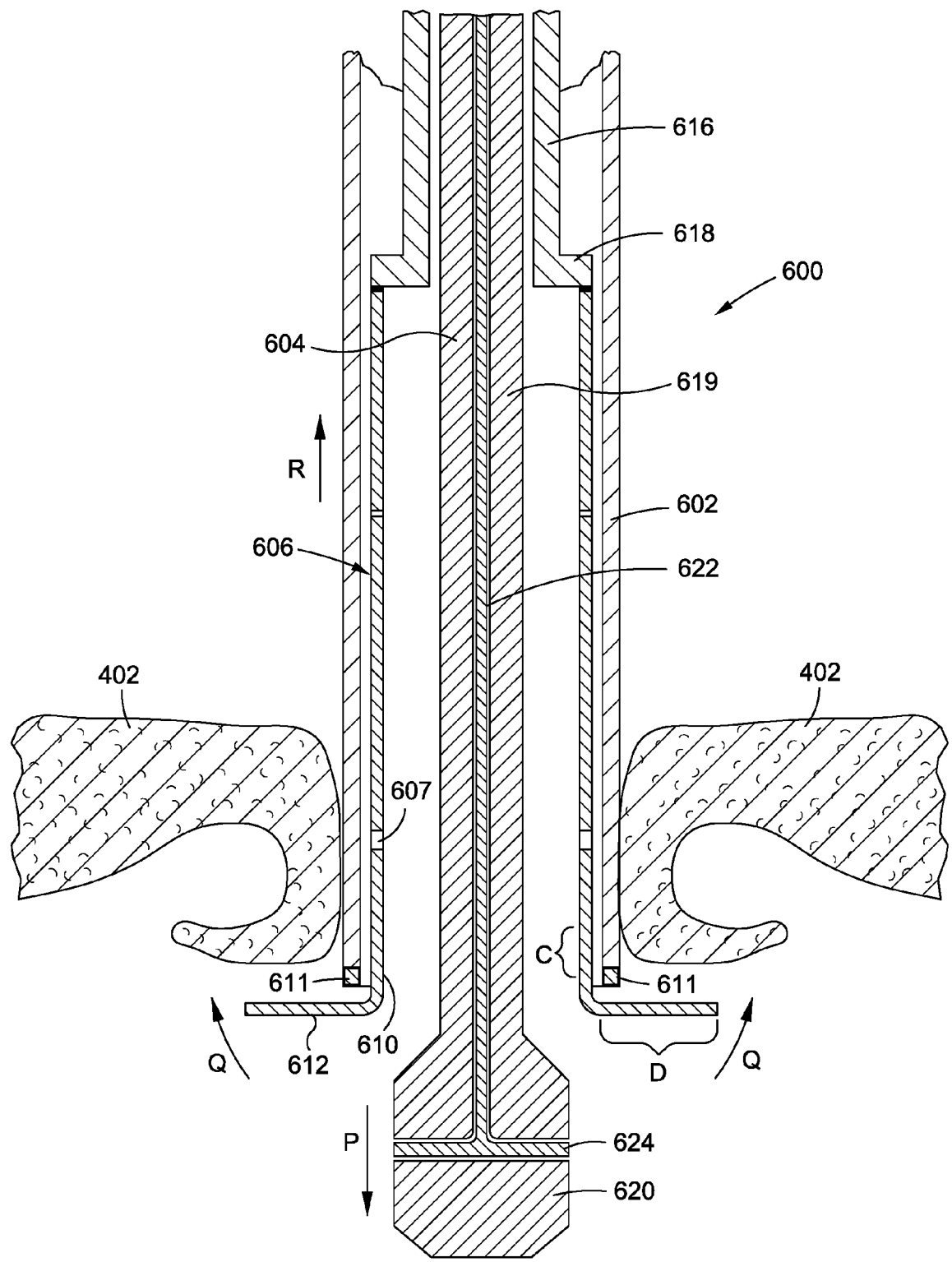
FIG. 5 is a sectional view of the catheter shown in FIG. 4, in a further condition of deployment.
Figure 6:
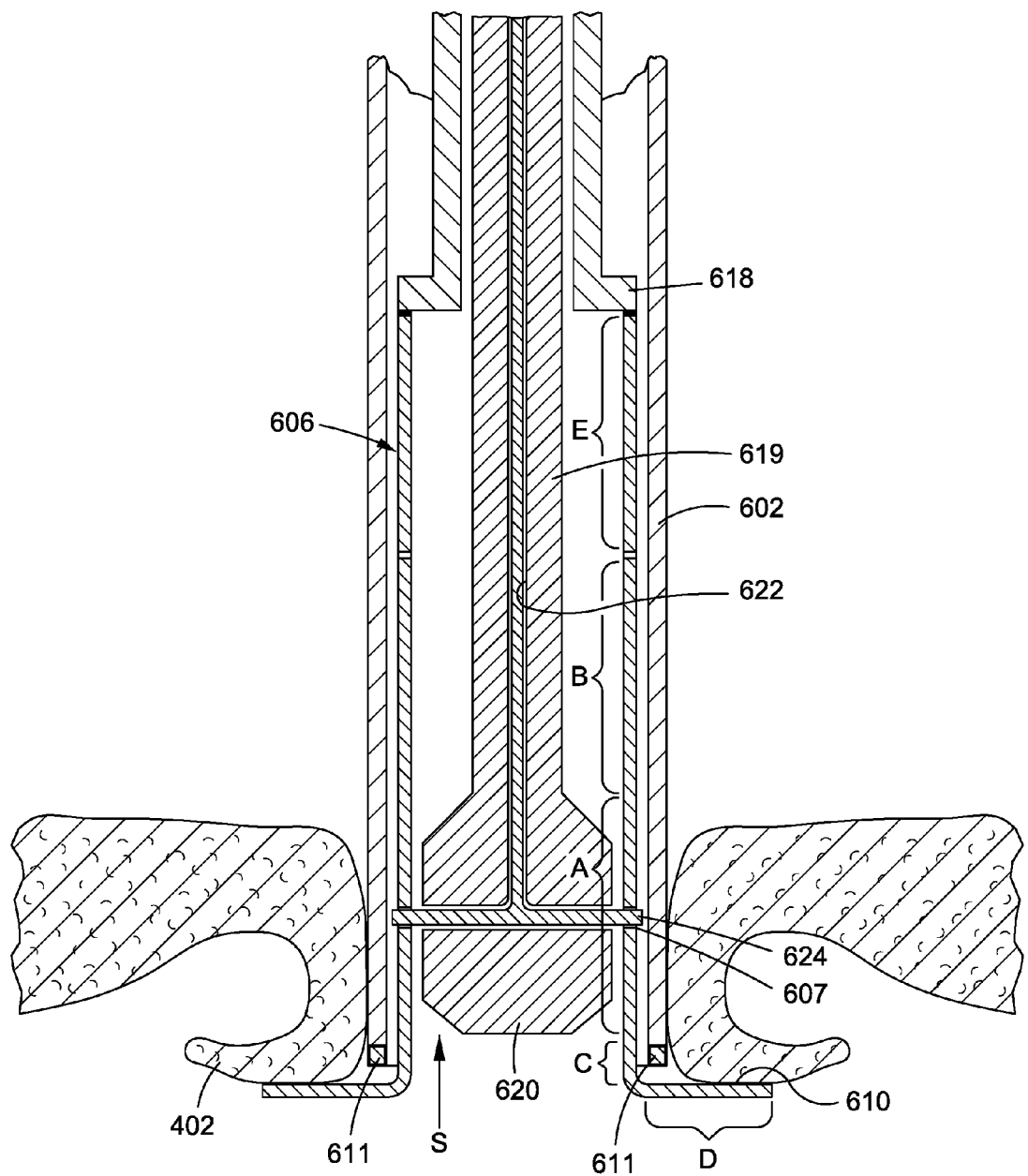
FIG. 6 is a sectional view of the catheter shown in FIG. 4, in yet a further condition of deployment.

The piston 620 includes additional structure that will be described in more detail with reference to FIG. 7A and FIG. 7B. For clarity, these aspects are omitted from FIG. 4 to FIG. 7A. The piston includes an internal piston lumen 622 that extends all the way back to the proximal end of the catheter via the rod 619. Within the piston lumen resides a set of retention pins 624 which are configured to be withdrawn inside the piston 620 as shown in FIGS. 4 and 5, or which can be activated to protrude beyond the external surface of the piston surface, as shown in FIGS. 6 and 7. The activation of the retention pins 624 to protrude beyond the surface of the piston 620 will be described in further detail below.

In use then, the distal end of the catheter 600 is pushed distally into the leaflets 402 of the mitral valve, as shown in FIG. 4. Then, as shown with reference to FIG. 5, the outer sheath is pulled proximally (arrow R) to expose the lower flange elements 610. The outer sheath is pulled no higher than this, so that the sheath acts as a confining ring around the base of the mesh elements 605, of Section A. In some embodiments, a stiff metal ring 611 is embedded in the distal end of the sheath 602. Then, the piston 620 is pushed via the rod 619 distally (arrow P), so that the piston 620 engages against the horizontally oriented transition elements 612 which are in Section C of the tube. Further distal movement of the piston forces the transition elements 612 to rotate away from their horizontal alignment and to bend in a downward direction; and this movement of the transition elements 612 forces the lower flange elements 610 to rotate radially outwardly and upwardly (arrow Q) until they are horizontally aligned, as shown in FIG. 5. This movement of the lower flange elements 612 brings them into contact with the leaflets 402 of the mitral valve, and moves them in an upward pinching movement. It will be appreciated by those of ordinary skill in the art that the presence of the ring 611 plays a useful role in preventing the struts 605 in Section A from expanding outwardly when the piston 620 is moved distally. The ring 611 compels only the transition elements 612 (Section C) to be plastically deformed during this action, so that the lower flange elements 610 are compelled to adopt a radially outwardly extending orientation and thus to tightly engage with the leaflets 402. In this regard, the ring 611 must be sufficiently stiff or resilient to contain and confine the tube so that the annular portion does not expand radially when the piston is moved to deform the transition elements. It will be appreciated that, without the resilient ring, the stiffness of the polymer sheath alone may not be sufficient to contain the annular portion during deformation of the transition elements. Hence, the ring 611 may be made of metal and installed at the distal end of the sheath so as to act as a hoop reinforcement to the distal end of the sheath.

Once this action is complete, the piston 620 is moved back proximally (arrow S) into its position within the mesh elements 605 of Section A, as shown in FIG. 6. At this point, the retention pins 624 are activated to protrude outside the surface of the piston 620. The pins are configured to be long enough to slide within an opening 607 formed by the mesh elements, and in this position will hold the tube 606 fixed in relation to the piston 620, able to withstand the next action.

Figure 7A:
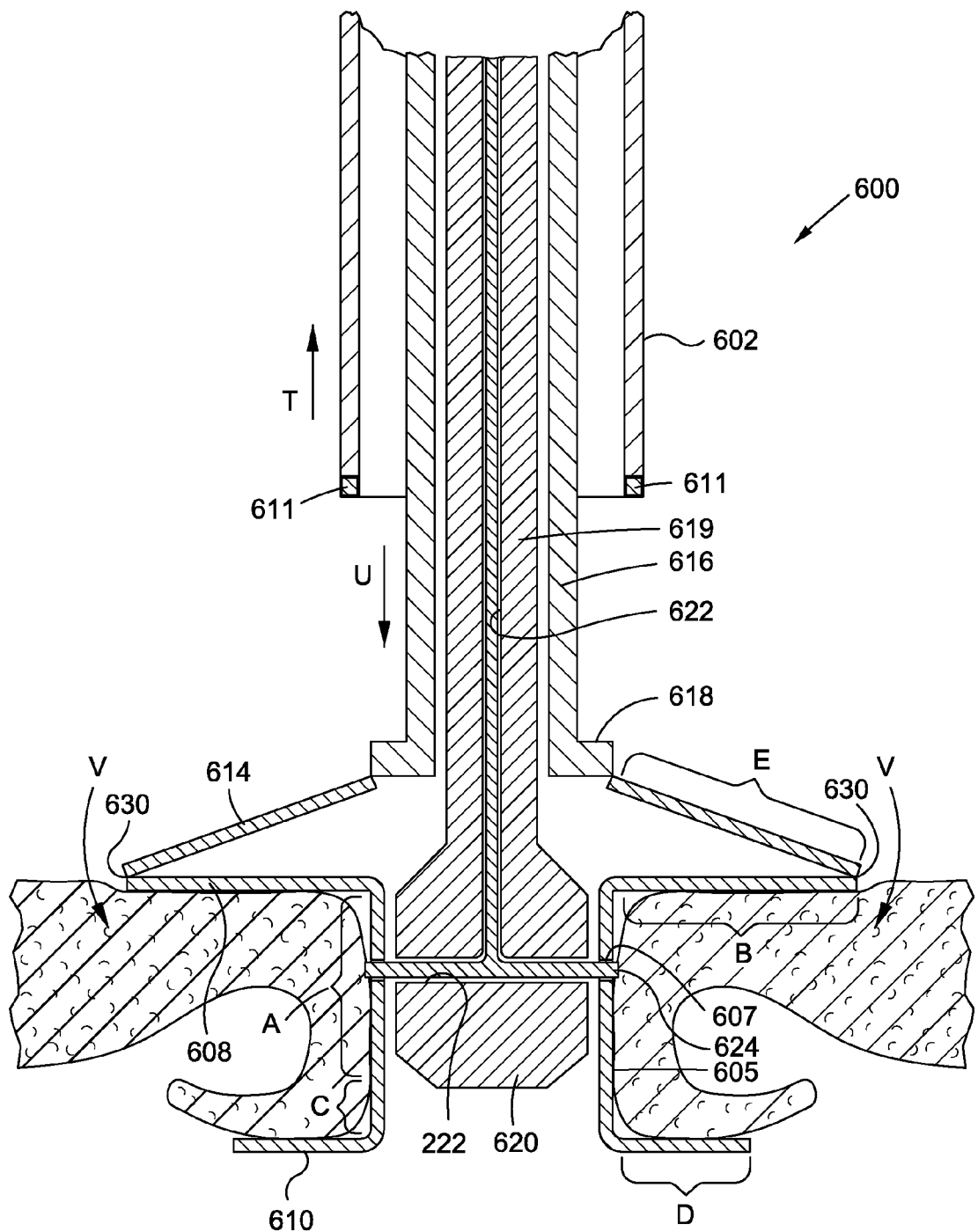
FIG. 7A is a sectional view of the catheter shown in FIG. 4, in an even further condition of deployment.

With reference to FIG. 7A, the sheath 602 is pulled further proximally (arrow T), which exposes both the push rods 614 of the tube, found in Section E, and also the upper flange elements 608, found in Section B. Once this action is complete, the pusher element 616 is advanced distally (arrow U, FIG. 7A). This action applies a compressive force on the push rods 614 (Section E) which in turn apply a compressive force on the upper flange elements 608 (Section B). The joint 630 (described in detail with reference to FIGS. 11A-11C) between the push rods 614 and the upper flange elements 608 provide a point at which the compressive force causes Section E and Section B to buckle at the joint (as exemplified in FIG. 7A, FIG. 7B, and FIG. 11C), and move radially away from the axis of the tube. At this stage, the upper flange elements 608 pinch down on the upper surface of the mitral valve annulus, and compress the leaves 402 so that the tube grips onto the annulus of the native valve.

Figure 11A:
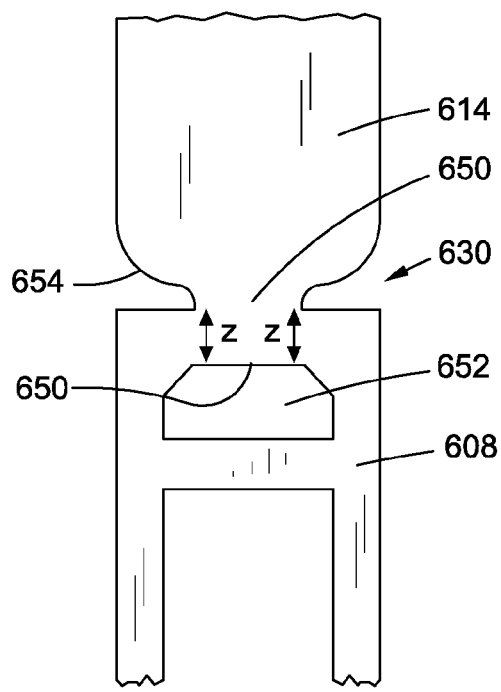
FIG. 11A is a front view of a detail of the area marked as "X" in FIG. 9.
Figure 11B:
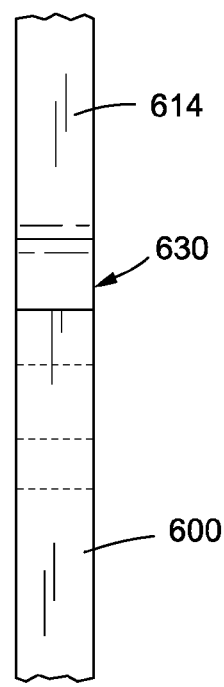
FIG. 11B is a side view of the detail view in FIG. 11A.
Figure 11C:
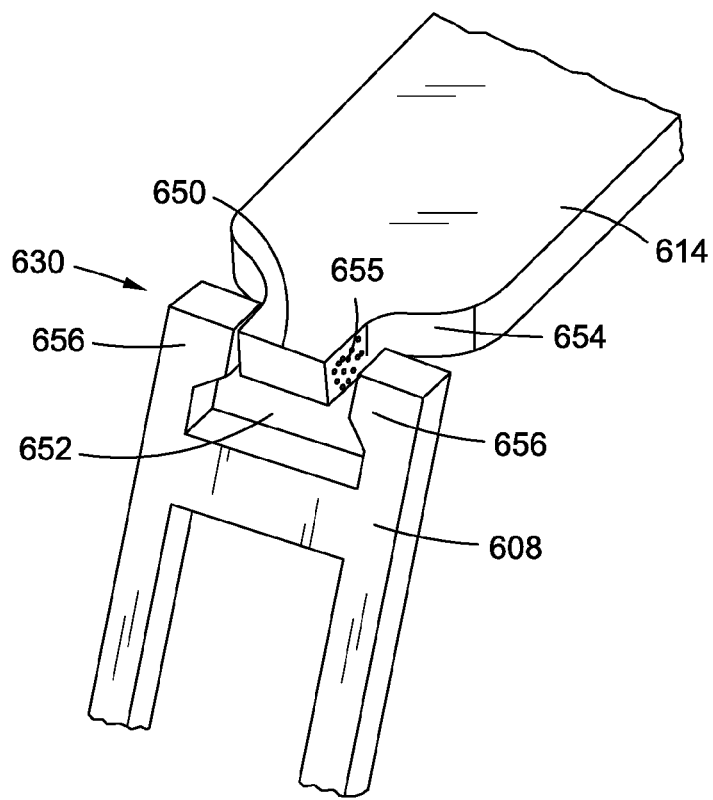
FIG. 11C is a perspective view of the detail view in FIG. 11A, shown in a bent configuration wherein one portion has become separated from another portion.

By way of detail clarification, and with reference to FIGS. 11A-11C, the joint 630 is further configured to fracture under torsional stress along a line identified by the letter Z in FIG. 11A which results in a fracture plane 655 as exemplified in FIG. 11C, after a certain amount of rotation of that joint. However, the joint is configured so that a narrow head 650 on the push rod 614 formed after the fracture falls into a slot 652 formed in the upper flange element 608. Shoulders 654 formed behind the head 650 are too broad to pass through the slot 652. Additionally, after the fracture, knuckles 656 on the upper flange element prevent the head 650 from sliding upward (proximally) in relation to the upper flange elements 608. For as long as the push rod 614 applies a distally directed compressive force on the proximal extremities of the upper flange element 608, the push rod and the upper flange element are linked together. Only when a proximal tensile force is applied to the push rods 614 can the head 650 become disengaged by withdrawing it out of the slot 652. These features provide a useful structure allowing the push rods 614 under compression to break away from the upper flange elements 608, yet remain linked together; while, under tension, the push rods 614 uncouple from the upper flange elements 608.

In some embodiments, the piston 620 may be configured to be expanded radially outwardly, to force a portion of the tube into closer engagement with the mitral annulus of the heart. FIG. 7B exemplifies features of an embodiment configured to accomplish this function. Here, the rod is divided into an outer rod 632 defining a lumen 633 and inner rod 634 configured to slide within the lumen 633. Both inner rod 634 and outer rod 632 extend all the way back to the proximal end of the catheter 600, and may be caused to slide in opposite directions to each other by the physician user using known control means at the proximal end of the catheter. The outer rod 632 terminates at its distal end in an upper plate 636. Movement of the outer rod causes equal movement of the upper plate 636. The inner rod 634 terminates at its distal end in a lower plate 638. Movement of the inner rod causes equal movement of the lower plate. Positioned between the two plates 636, 638, and in contact with both plates, is an expander piece 621. The expander piece 621 is formed from a malleable material such as rubber or polymer with a high Poisson's ratio. When Section A (also referred to herein as the annular section) is positioned in the desired location in relation to the leaves 402 of mitral annulus, the physician user may elect to expand the diameter of Section A to come into tighter contact with the mitral annulus. Such expansion is achieved by moving the inner rod 634 proximally while moving the outer rod 632 distally. This movement causes the two plates 636, 638 to squeeze towards each other and thus to apply an axially compressive force on the expander piece 621. Due to the high Poisson's ratio of the material forming the expander piece 621, the expander piece expands radially outwardly and applies a radial outward force on the annular portion (Section A). It will be appreciated that the shape of the struts 605 making up the annular portion allows plastic deformation of the metal making up the struts to take place, under which the diameter of the annular portion is permanently expanded and remains so expanded when the piston is eventually removed. This aspect allows the physician user to conveniently expand the annular portion to take up any free space, and implant the annular portion tightly within the mitral annulus.

Figure 7B:
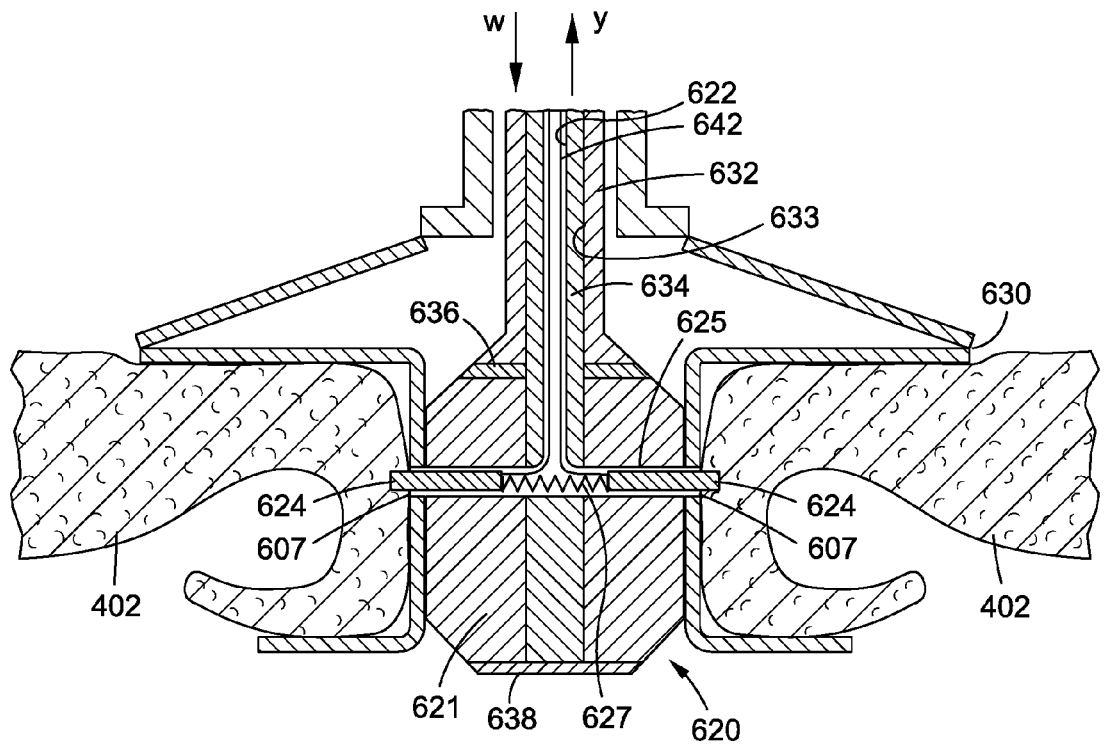
FIG. 7B is an enlarged view of a portion of the view of FIG. 7A, showing more structural detail.

A further detail shown in FIG. 7B exemplifies an actuation mechanism for the restraining pins 624. These pins reside at opposite ends of a transverse lumen 625 extending from one side of the expander element 621 to the other. A spring 627 forces the pins apart, so that without a retracting force, the pins are biased to extend out of the ends of the lumen 625. An actuation wire 642 extends down the lumen 622, and splits into two wires at the point of connection with the transverse lumen 625, one of the two wires extending to connect with a left pin 624 and the other extending to connect with a right pin 624, so that proximal movement of the actuation wire 642 causes both left pin and right pin to retract into the lumen 625. The retraction wire is operable at the proximal end of the catheter according to known means. Thus, the physician user may extend or retract the pins 624 according to the stage of deployment of the annular portion.

Figure 8:
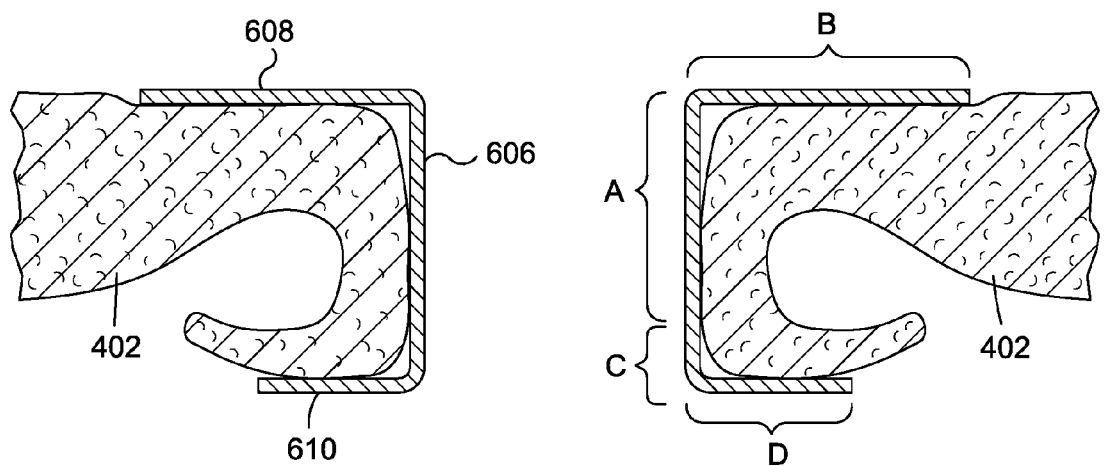
FIG. 8 is a sectional view of a component of the structures shown in FIG. 4-FIG. 7B having been deployed into the annulus of a mitral valve of a patient according to an embodiment of the invention.

Once the pusher element 616 has been advanced to bend the upper flange elements 608 normal to the tube axis, the pins are withdrawn into the expander element, the catheter 600 is withdrawn proximally, thereby extracting the heads 650 on the pull rods 614 from the slots 652 of the upper flange elements 608. The catheter 600 is pulled proximally, thus withdrawing the expander element. This action leaves behind a deployed portion of the tube, made up of Sections A, B, C, and D as exemplified in FIG. 8.

The deployed portion now consists of an upper flange (Section B), a lower flange (Section D), and a central bore (Sections A and C) and these elements taken together now constitute an annular platform. This annular platform may, in some embodiments, be expanded by an expander element 621 to press tightly against the tissue forming the mitral annulus of the patient's heart as described. The deployed portion forms a stable annular platform for subsequently inserting a prosthetic mitral valve of any kind that is available on the market.

Thus, the system and method of the invention addresses problems identified in the art, and other problems. The platform provided is rigid, having been plastically deformed into position. It is sized to correctly fit the tissue of the native mitral annulus.

Although preferred illustrative variations of the present invention are described above, it will be apparent to those skilled in the art that various changes and modifications may be made thereto without departing from the invention. For example, it will be appreciated that combinations of the features of different embodiments may be combined to form another embodiment. The invention itself is as described in the claims.

I claim:

1. A system for delivering a platform to support a prosthetic mitral valve in a patient's heart, the system comprising:
    a delivery catheter that includes a slidable sheath;
    a tube positioned within the slidable sheath defining a structure that includes:
        an annular portion defining a bore and an axis that extends along the bore, and further defining at least one opening in a circumferential surface of the annular portion,
        a plurality of upper elements attached to an upper perimeter of the annular portion and extending axially, and
        a plurality of lower elements attached to a lower perimeter of the annular portion and extending axially; and
    a piston configured to slide within the tube, the piston defining a lumen that receives at least one pin configured to slide out of the lumen so as to pass through the at least one opening; and
    wherein the slidable sheath includes a resilient ring at a distal end of the slidable sheath.

2. The system of claim 1, wherein the at least one pin includes two pins, and the two pins are separated from each other by a spring configured to urge the two pins apart from each other.

3. The system of claim 2, wherein each pin is attached to a retraction wire that extends inside the lumen, the retraction wire being attached to each of the two pins, whereby the two pins are urged towards each other when the retraction wire is pulled proximally.

4. The system of claim 1, wherein the resilient ring is made of metal.

5. The system of claim 1, wherein the annular portion occupies a first cylindrical profile having a first diameter, and the plurality of lower elements occupy a second cylindrical profile having a second diameter smaller than the first diameter.

6. The system of claim 5, wherein the piston has an outer circumferential surface having a third diameter that is smaller than the first diameter but larger than the second diameter, whereby distal movement of the piston applies a force against the plurality of lower elements thus to urge each of the plurality of lower elements to bend away from the axis.

7. The system of claim 1, wherein the piston includes a means for causing the circumferential surface to expand.

8. The system of claim 1, further including a means for applying a distal force against a proximal end of each of the plurality of upper elements and thus to urge the plurality of upper elements to bend away from the axis.

9. A method for delivering a platform for reinforcing an annulus of a mitral valve in a heart of a patient, the heart including a right atrium, a left atrium, and a septum separating the right atrium from the left atrium, the method comprising:
    providing a delivery system having:
        a delivery catheter that includes a slidable sheath,
        a tube positioned within the slidable sheath defining a structure that includes:
            an annular portion defining a bore and an axis that extends along the bore, and further defining at least one opening in a circumferential surface of the annular portion,
            a plurality of upper elements attached to an upper perimeter of the annular portion and extending axially, and
            a plurality of lower elements attached to a lower perimeter of the annular portion and extending axially, and
        a piston configured to slide within the tube, the piston defining a lumen that receives at least one pin configured to slide out of the lumen so as to pass through the at least one opening,
        wherein the slidable sheath includes a resilient ring at a distal end of the slidable sheath;
    passing, via a femoral artery of a patient, the catheter into the right atrium, then through the septum into the left atrium,
    withdrawing the sheath from covering the plurality lower elements, but leaving the sheath covering the annular portion and the plurality of upper elements;
    bending the plurality of lower elements by imparting a plastic deformation to the metal until the plurality of lower elements extend radially so as to be positioned beneath the mitral valve;
    then withdrawing the sheath from covering the annular portion and the plurality of upper elements; and
    bending the plurality of upper elements by imparting a plastic deformation to the metal until each of the plurality of upper elements extends radially so as to be positioned above the mitral valve.

10. The method of claim 9, wherein the annular portion occupies a first cylindrical profile having a first diameter, and the plurality of lower elements prior to being bent occupy a second cylindrical profile having a second diameter smaller than the first diameter, and wherein bending the plurality of lower elements includes moving the piston distally through the annular portion and engaging each of the plurality of lower elements with the piston, the piston having a third diameter greater than the second diameter.

11. The method of claim 10, wherein moving the piston distally through the annular portion and engaging each of the plurality of lower elements with the piston is simultaneously accompanied by restraining the first diameter of the annular portion against expansion.

12. The method of claim 11, wherein restraining the annular portion against expansion of the first diameter includes positioning the resilient ring around the lower perimeter of the annular portion.

13. The method of claim 12, wherein positioning the resilient ring includes positioning a distal end of the sheath around the lower perimeter of the annular portion.

14. The method of claim 10, further including expanding the first diameter of the annular portion by imparting a plastic deformation to the metal.

15. The method of claim 14, wherein expanding the first diameter of the annular portion includes expanding the first diameter until the annular portion is in contact with the annulus of the mitral valve along a continuous circumference of the annular portion.

16. The method of claim 14, wherein expanding the first diameter of the annular portion includes expanding the third diameter of the piston.

17. The method of claim 9, wherein bending the plurality of upper elements includes applying an axially oriented force on each of the plurality of upper elements.

18. The method of claim 17 further including applying a force having a radially outward component to each of the plurality of upper elements.

19. The method of claim 18, wherein applying a force having a radially outward component to each of the plurality of upper elements includes applying a moving force to a proximal extremity of each of the plurality of upper elements.

20. The method of claim 17, wherein applying an axially oriented force includes applying a force to a proximal extremity of each of the plurality of upper elements.

21. The method of claim 17, wherein applying an axially oriented force includes restraining the annular portion against distal movement.

22. The method of claim 21, wherein restraining the annular portion against distal movement includes inserting a pin into the at least one opening.

* * * * *